United States Patent [19]
Massig et al.

[11] Patent Number: 5,321,446
[45] Date of Patent: Jun. 14, 1994

[54] SLIT LAMP MICROSCOPE AND SELECTIVELY INSERTABLE DIAPHRAGM DISK

[75] Inventors: Jurgen Massig, Essingen; Gerhard Gaida, Aalen, both of Fed. Rep. of Germany

[73] Assignee: Carl Zeiss-Stiftung, Heidenheim, Fed. Rep. of Germany

[21] Appl. No.: 21,335

[22] Filed: Feb. 23, 1993

[30] Foreign Application Priority Data

Feb. 26, 1992 [DE] Fed. Rep. of Germany ....... 4205865

[51] Int. Cl.⁵ .................... A61B 3/10; G02B 21/22
[52] U.S. Cl. .................... 351/214; 351/215; 359/235; 359/377
[58] Field of Search ............... 351/205, 214, 216, 217, 351/215; 359/235, 377

[56] References Cited

U.S. PATENT DOCUMENTS

| | | | |
|---|---|---|---|
| 3,926,500 | 12/1975 | Frosch et al. | 359/235 |
| 4,170,398 | 10/1979 | Koester | 351/211 X |
| 4,884,880 | 12/1989 | Lichtman et al. | 359/227 |
| 4,900,145 | 2/1990 | Akiyama | 351/221 |
| 4,927,254 | 5/1990 | Kino et al. | 359/235 |
| 5,020,891 | 6/1991 | Lichtman et al. | 359/235 |
| 5,099,354 | 3/1992 | Lichtman et al. | 359/227 X |

FOREIGN PATENT DOCUMENTS 3714041 11/1988 Fed. Rep. of Germany .

OTHER PUBLICATIONS

Kino, Gordon S. and Corle, Timothy R., "Confocal Scanning Optical Microscopy" *Physics Today*, Sep. 1989 pp. 55–62.

Müller, Ortwin *Ocular Examination with the Slit Lamp*, Zeiss, West Germany K-30-115e, MA-H-111/83 Koo (no date).

*Primary Examiner*—William L. Sikes
*Assistant Examiner*—David R. Parsons

[57] ABSTRACT

In a slit lamp microscope, changeover can be selectively made between conventional slit lamp microscopy and confocal perforated disk microscopy. In slit lamp operation, the microscope is constructed as a stereo microscope. The Nipkow perforated disk required for the confocal perforated disk microscopy is arranged in an indirect beam path. Alternatively, the Nipkow disk can be arranged on a pivotable support element and can be pivoted into the beam path in the vicinity of an intermediate image plane. For confocal perforated disk microscopy, an additional illumination device is provided that is reflected into the beam path between the Nipkow disk and the oculars. The insertion of the Nipkow disk or the switching of the beam paths takes place such that the focal plane of the objective is constant. A changeover is made from conventional slit lamp microscopy to confocal perforated disk microscopy without refocusing. A direct comparison of the images observed with the two procedures is therefore possible.

15 Claims, 3 Drawing Sheets

SLIT LAMP MICROSCOPE AND SELECTIVELY INSERTABLE DIAPHRAGM DISK

BACKGROUND OF THE INVENTION AND RELEVANT PRIOR ART

This invention relates to slit lamp microscopes. Slit lamp microscopes are principally used for the examination of the anterior eye regions of subjects. They usually consist of a slit illumination means that projects a slit-shaped spot of light into the eye of the subject and a stereo microscope with which the examining doctor observes the slit image. The microscope and the slit illumination means are mounted on a special slit lamp device base with which the slit lamp and the microscope can be simultaneously aligned with the eye of the subject. The chin rest for the subject is also arranged on the device base. Such slit lamp microscopes are described, for example, in the brochure "Ocular Examination with the Slit Lamp" with the printer's imprint K30-115-E-MAII/81 NOO.

Slit lamp microscopes have been used for a long time in ophthalmology, so that ophthalmologists already possess much experience in diagnosing eye diseases by means of the slit images observed with the stereo microscope. However, it is disadvantageous that the observed images are composed of light reflections and scattered light from different depth regions of the eye. The observation of individual, special planes is not possible with such slit lamp microscopes.

The return reflections from the cornea of the subject's eye using equipment in which the slit illumination is projected coaxially with the observation beam path has been found to be particularly trouble some. The relatively strong corneal reflection is then superimposed on the image of the interior of the eye. It is therefore proposed in German Offenlegungsschrift 3,714,041 to arrange a slit diaphragm that corresponds to the slit diaphragm on the illumination side in an intermediate image plane in the neighborhood of the ocular of the microscope. The corneal reflection is to be filtered out by the slit diaphragm arranged in the region of the ocular. By synchronous motion of the slit diaphragm on the illumination side and the slit diaphragm on the observation side, different regions of the subject's eye can be illuminated and observed. The observation of sectional planes of the subject's eye perpendicular to the axis of the eye is, however, not possible with this apparatus, because the slit diaphragms have a depth selective action only perpendicularly of the slit direction. Moreover, the conventional slit lamp illumination in which the slit is projected obliquely of the axis or of the axes of the microscope is not possible with this special equipment.

For examination of the background of the eye, an ophthalmoscope is known, for example, from U.S. Pat. No. 4,900,145, which consists of a conventional slit lamp and a microscope, and in which, in addition, a laser beam is reflected into the beam path of the slit lamp and is focused in the patient's eye. The back-scattered laser light is reflected onto a detector within the microscope. A slit diaphragm is furthermore arranged before the detector, in order to suppress undesired scattered light. The conventional slit illumination is used solely to determine the position of the laser focus within the eye. Thus slit illumination and laser beam illumination are conducted in a common beam path. Even this apparatus does not make possible the visual observation of given sectional planes within the subject's eye.

In conventional microscopy, so-called Nipkow microscopes are known, for example from U.S. Pat. No. 3,926,500; U.S. Pat. No. 4,884,880; and U.S. Pat. No. 4,927,254; and the article "Confocal Scanning Optical Microscopy" in Physics Today, September 1989, pp. 55-62. In such Nipkow microscopes, a Nipkow disk is rotatingly arranged in an intermediate image plane between the objective and the oculars. The Nipkow disk itself is opaque and has a large number of transparent holes arranged along several Archimedean spirals. Each of these transparent holes then acts simultaneously as a confocal illumination and observation diaphragm. Thus the result is that essentially only the light scattered or reflected into a plane conjugate to the plane of the Nipkow disk is transmitted through the holes of the Nipkow disk and hence reaches the ocular. A pointwise assembled image of a special sectional plane thus arises in the ocular. The individual transparent holes are moved through the image field by rotation of the Nipkow disk, so that with a sufficiently dense arrangement of the spirals and with a sufficiently high rate of revolution of the Nipkow disk a stationary, flicker-free image of a depth section is generated.

The use of such Nipkow microscopes in opthalmoscopy is still quite unknown. Hence it is very difficult for the ophthalmologist to diagnose eye diseases on the basis of depth sections through the eye observed with a Nipkow microscope.

SUMMARY OF THE INVENTION

It is therefore the object of the present invention to make available an ophthalmological device with which visual observation is possible of special depth sections within the eye being examined, and with which the existing experience in conventional ophthalmoscopy can be used in the best possible way.

This object is achieved according to the invention by a slit lamp microscope having a slit lamp for the projection of a slit-shaped spot of illumination onto the eye of a subject, a microscope with at least one objective, at least two oculars and at least one beam path running between the objective and the oculars, and a diaphragm disk arranged in or in the vicinity of an intermediate image plane in the beam path and having numerous transparent and opaque regions, with the transparent regions scanning the image in the intermediate image plane.

By the combination of a slit lamp on the one hand and a Nipkow microscope on the other hand, a special slit lamp microscope is provided with which there is possible both conventional slit lamp microscopy, namely with the slit lamp inserted, and also the visual observation of defined depth sections. Hence it is possible for the ophthalmologist to compare, in rapid succession, directly in a single equipment and by looking into the same ocular, the observed depth sections and the images known to him of slit lamp microscopy. The ophthalmologist can thus fully use the experience he has obtained in slit lamp microscopy.

In preferred embodiments, the diaphragm disk, preferably formed as a Nipkow disk, can be selectively inserted into and out of the beam path. Inserting the Nipkow disk into or out of the beam path can be achieved directly by a motion of the Nipkow disk, for example, a pivoting motion. However, it is also possible to provide several beam paths and to arrange the Nipkow disk in one of these beam paths. Then the Nipkow disk is switched in by deflecting the observation beam path along the respective beam path in which the Nipkow disk is arranged. Corresponding movable deflecting means, such as mirrors or prisms, are provided for the deflection of the beam path. The Nipkow disk is switched out if the light is conducted over the other beam path, and any depth filtering effected by the Nipkow disk is likewise eliminated. Exactly the same image is presented to the opthalmologist, with the slit illumination inserted and the Nipkow disk simultaneously taken out, as is presented to him with a conventional slit lamp microscope.

To reinforce the depth-selective action of the Nipkow disk, the illumination beam path should be led through the Nipkow disk itself, when the Nipkow disk is inserted. A second illuminating device is preferably provided for this purpose and is reflected into the beam path between the Nipkow disk and the oculars. The insertion of this second illumination device preferably takes place coupled with the insertion of the Nipkow disk. A coupling of the Nipkow disk to the slit lamp is also simultaneously provided, so that the slit lamp is automatically taken out when the Nipkow disk is inserted.

In the embodiment in which, for insertion, the Nipkow disk is itself moved relative to the beam path, the Nipkow disk is arranged, with an associated drive motor and also the additional illumination device and a partially reflecting mirror, on a movable change element. On moving in the Nipkow disk, the beam splitter is simultaneously moved in, for reflecting the additional illumination into the beam path between the Nipkow disk and the ocular, and is moved out of the beam path when the Nipkow disk is moved out. The result achieved is that, with the Nipkow disk moved out, the same observation light reaches the ocular.

However, the embodiment is particularly advantageous in which the Nipkow disk is arranged in an indirect beam path. The deflecting elements required for the deflection of the beam path are then preferably arranged on a rotary element, which is rotatable about an axis which is perpendicular to the optical axis of the objective and perpendicular to the axis of the indirect beam path. Additional optical elements, for example a lens system forming a Gallilean telescope with different magnifications, can be arranged on this rotary element. Actuation of the rotary element makes it possible to change over to different magnifications in conventional slit lamp microscopy and to confocal microscopy.

The slit illumination is preferably arranged in a second housing portion with a separate illumination beam path. The housing of the microscope and the housing of the slit lamp are furthermore preferably rotatable on a base about a common axis in the focal plane of the objective. In this manner, different angles can be set between the slit illumination and the microscopic observation, and also different observation angles relative to the subject's eye.

The microscope is preferably a stereo microscope, because stereo microscopes facilitate the best possible observation of the slit image in conventional slit lamp microscopy. A common main objective is then preferably provided for both stereo channels. In the operation of the microscope as a confocal perforated plate microscope, the imaging results via a central region of the main objective, concentric with the optic axis. Special means for the superposition of both stereo channels are therefore not necessary.

DESCRIPTION OF THE DRAWINGS

Particulars of the invention are explained below in more detail with reference to preferred embodiments illustrated in the accompanying drawings, in which.

DETAILED DESCRIPTION OF PREFERRED EMBODIMENTS

Figure 1A:
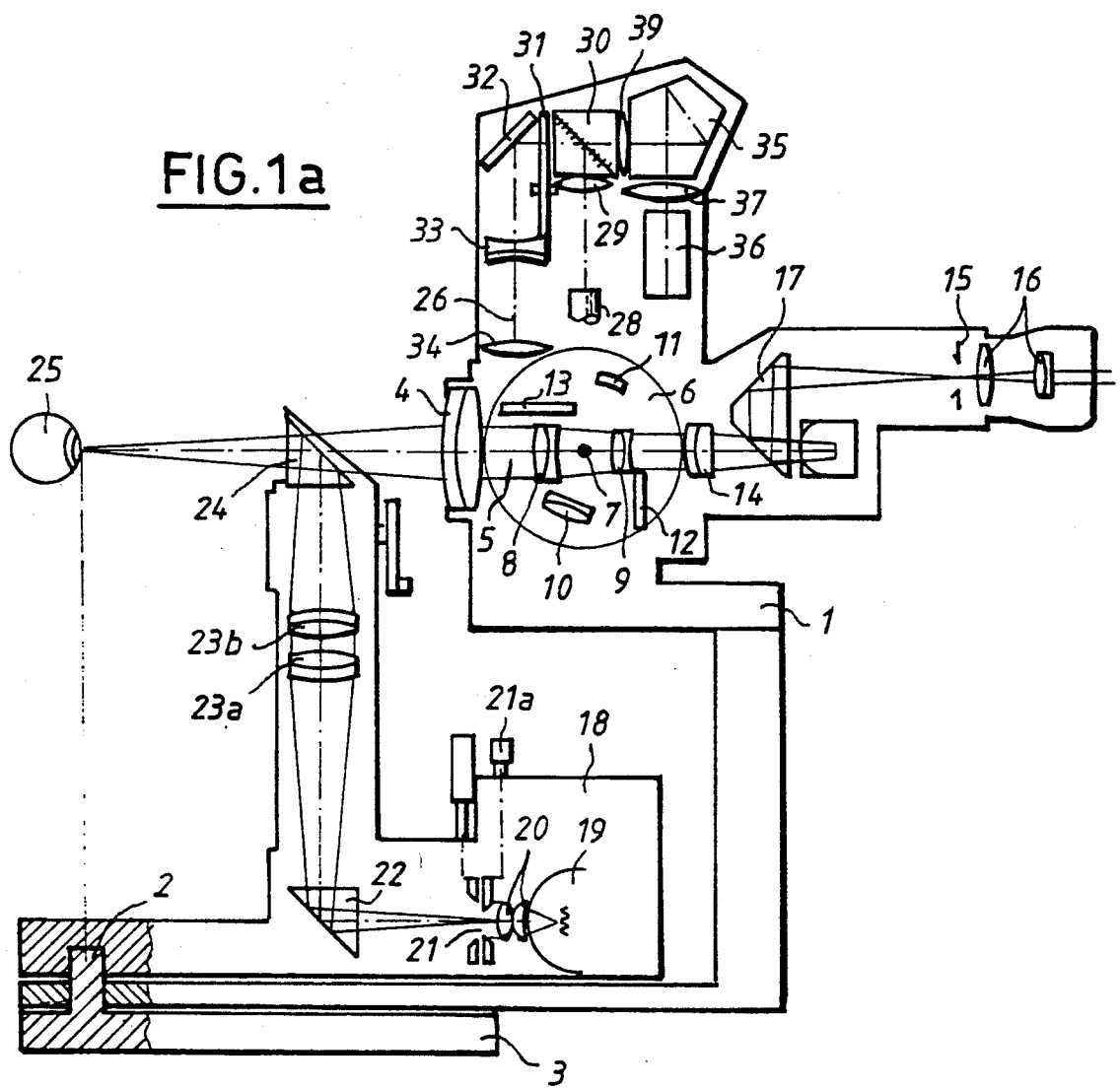
FIG. 1a is a vertical schematic through a first embodiment according to the invention, during operation as a slit lamp microscope.
Figure 2A:
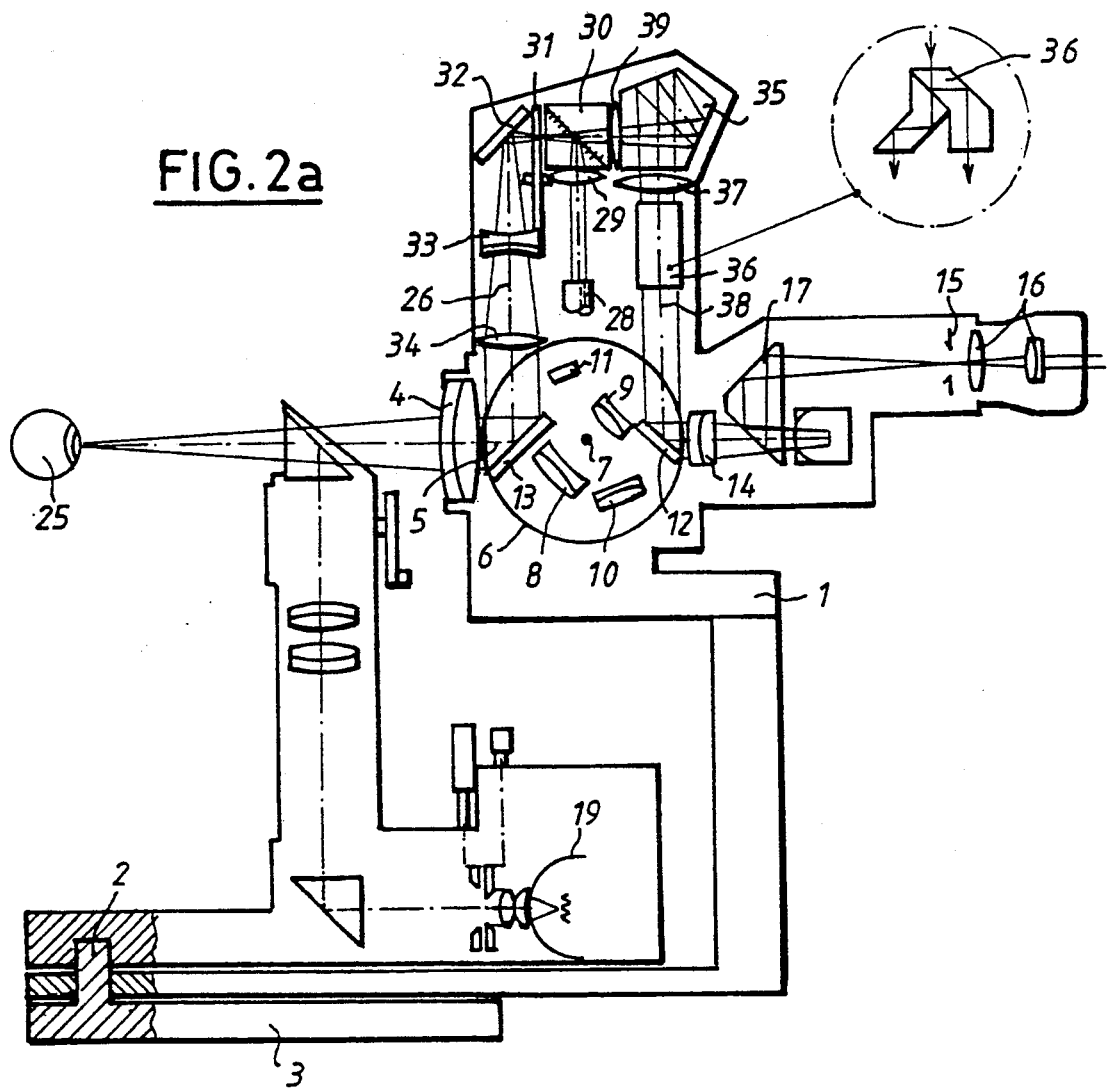
FIG. 2a is a vertical schematic through the slit lamp microscope of FIG. 1a, during use as a confocal perforated plate microscope.

The slit lamp microscope shown in FIGS. 1a and 2a has a first housing portion (1), which is arranged, rotatable about a vertical axis (2) on a device base (3). A stereo microscope with a common main objective (4) is arranged in the housing portion (1).

The main objective (4) is infinity-corrected so that the beam paths (5) of both stereo channels, seen in the direction of observation, run telecentrically behind the main objective (4).

Lens systems (8, 9, 10, 11) for each stereo channel, respectively pairwise representing a Gallilean telescope, are arranged on a support element (6) that is rotatable about a horizontal axis (7). This rotatable support element (6) has three switching positions. In a first switching position, the two lens systems (8, 9) are arranged in the beam path and in common represent a quite weak Gallilean telescope. In a second switching position the two lens systems (10, 11), which are opposed relative to the axis of rotation (7), can be moved into the beam path, and together represent a Gallilean telescope of greater magnification. As will be more fully explained in connection with FIG. 1b, each lens system (8, 9, 10, 11) is separately provided for each stereo channel. In a third switching position, two full mirrors (12, 13) can be moved into the beam path. In this third switching position, the microscope is operated as a binocular confocal microscope, as will be described in more detail with reference to FIG. 2a and 2b. A respective tube lens (14) is arranged behind the rotary element (6) in each stereo beam path and produces a real image in an intermediate image plane (15) in front of the oculars (16). Porro systems of prisms (17) for image erection are arranged between the tube lenses (14) and the oculars (16).

A slit lamp projector is arranged in a second housing portion (18), which is likewise arranged on the base (3) to be rotatable about the axis (2). The slit lamp housing (18) contains a light source (19) and a collector (20) for uniform illumination of a slit (21). The slit (21) is adjustable by means of positioning elements (21a). A prism (22) deflects into a vertical region the light that leaves the slit (21) essentially horizontal. A projection system consisting of two lens groups (23a, 23b) is arranged in the vertical region of the beam path. This projection system (23a, 23b) images the slit (21) via a further deflecting prism (24) into the subject's eye (25) to be examined. A headrest, not shown, ensures that the subject's eye (25) is arranged substantially vertically above the extension of the common axis of rotation (2) of both housing portions (1, 18). Different angles between the direction of illumination and the direction of rotation can be set by rotation of the microscope housing (1) and the slit lamp housing (18). Moreover, different illumination and observation angles relative to the optical axis, not shown, of the subject's eye (25) can be set by rotation of both housing portions (1, 18) in common.

Figure 1B:
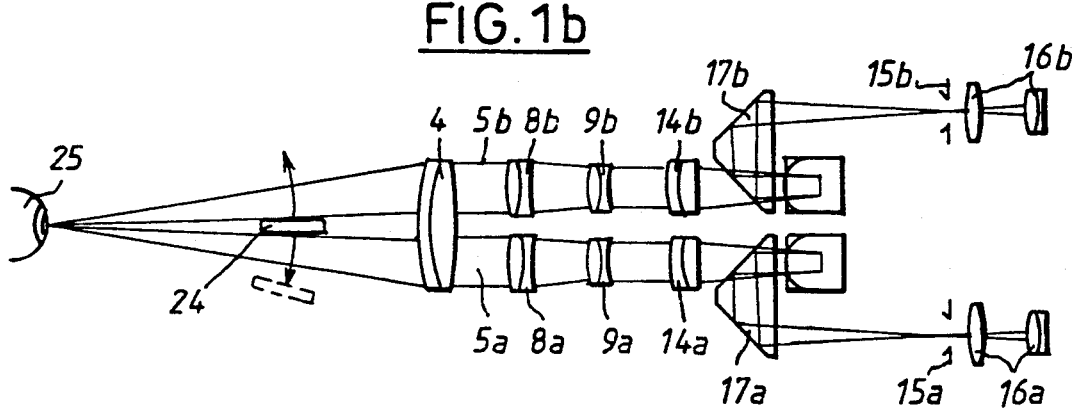
FIG. 1b is a schematic showing in principle the beam paths of the embodiment of FIG. 1a, projected onto a horizontal plane.

In FIG. 1b, in which the observation beam paths are shown projected onto a horizontal plane, components identical to those in FIG. 1a are given identical reference numbers. A left-hand (5a) and a right-hand (5b) stereo channel are formed by the prismatic action of the main objective (4). All the optical components which are arranged between the main objective (4) and the oculars (16a, 16b) are present separately for each stereo channel (5a, 5b). The components of the left-hand stereo channel are respectively denoted by an index a and the components of the right-hand stereo channel respectively by an index b. Behind the main objective (4) there are first arranged identical Gallilean telescopes (8a, 9a; 8b, 9b) in each stereo channel. Two identical tube lenses (14a, 14b) respectively produce a real intermediate image in an intermediate image plane (15a, 15b) of each stereo channel, the left-hand intermediate image (15a) being observable through the left-hand ocular (16a) and the right-hand intermediate image (15b) through the right-hand ocular (16b). A further image-erecting Porro prism system (17a, 17b) is arranged between the tube lenses (14a, 14b) in each stereo channel. The deflecting prism (24) of the slit illumination is shown between the main objective (4) and the subject's eye (25). By pivoting the slit lamp housing about the axis (2) (FIG. 1a), the angle between the slit illumination and the two stereo channels can be varied. This is indicated by the two arrows.

An indirect beam path (26) is arranged above the rotary element (6), as can be seen in FIG. 1a. The observation beam path is conducted over this indirect beam path (26) when the slit lamp microscope is operated as a confocal perforated disk microscope. The changeover between slit lamp microscope on the one hand and confocal perforated disk microscope on the other hand takes place by a rotation of the rotary element (6) so that the full mirrors (12, 13) are pivoted into the beam path. The rotary element (6) is coupled to a switch, not further described here, which has the effect that when operating as a confocal Nipkow disk microscope the light source (19) of the slit lamp is switched off, and simultaneously the additional illumination (28) is switched on.

The same microscope is depicted in FIG. 2a, during operation as a confocal perforated disk microscope. A glass fiber illumination means (28), which is supplied with light by an external supply device, not shown, acts as the light source for this operation of the microscope. The light emerging from the glass fiber bundle (28) is reflected into the indirect beam path (26) behind a lens (29) of a polarization beam splitter (30). A Nipkow disk (31) rotating about a horizontal axis is arranged behind the beam splitter (30). The rotational motion of the Nipkow disk (31) is produced by a drive motor, not shown here. It is not necessary to go further here into the Nipkow disk itself and its drive, since such Nipkow disks, with numerous round holes of respectively equal diameter and arranged in spirals, are known from the documents concerning Nipkow disk microscopes, especially U.S. Pat. No. 4,927,254, cited at the beginning.

The polarization beam splitter (30) acts so that only linearly polarized light whose direction of polarization lies in the incidence plane of the polarization beam splitter (30) reaches the Nipkow disk (31). The disturbing light reflected from the Nipkow disk (31) has the same direction of polarization. It is therefore reflected by the polarization beam splitter (30) to the optical waveguide (28) and consequently cannot reach the observer. This arrangement has a side effect, which is frequently desired for the use provided: the usually disturbing light originating from the reflection from the front of the cornea has the same direction of polarization as the light reflected on the Nipkow disk and therefore likewise does not reach the observer. The light coming from the interior of the cornea or the parts of the subject's eye (25) that lie deeper has an altered state of polarization, caused by double refraction of the cornea or by depolarization during back-scattering, and therefore can be observed. If this side effect is undesired, it can be eliminated, as in the known antireflection arrangement for reflected light microscopes, by the insertion of a quarter-wavelength delay plate between the objective (4) and the subject's eye (25) or at a suitable place between the objective (4) and the Nipkow disk (31).

For further suppression of the reflections of the Nipkow disk (31), its axis can be slightly inclined to the optical axis, so that the reflected light meets a suitably arranged diaphragm in the beam path between the lens (39) and the oculars (16a) and (16b). Regard must be paid to the fact that this inclination of the Nipkow disk (31) results, according to the Scheimpflug principle, in a slight inclination of the observed conjugate plane in the subject's eye (25). This is of course of no importance for the envisaged use.

A mirror (32) arranged behind the Nipkow disk (31) deflects vertically downwards the light transmitted through the transparent holes of the Nipkow disk (31). A tele-objective (33, 34) images the Nipkow disk (31) at infinity, and the full mirror (13) arranged on the rotary element (6) deflects the light to the main objective (4). The main objective (4) produces an image of the Nipkow disk (31) in the interior of the subject's eye (25).

The light scattered or reflected in or on the subject's eye (25) is in itself reflected back by the objective (4) via the deflecting mirror (13, 32) and the tele-objective (33, 34) and is imaged on the Nipkow disk (31). Essentially only that light can pass through the transparent holes of the Nipkow disk that has been reflected or scattered in a plane within the subject's eye (25) conjugate to the Nipkow disk (31). The light reflected or scattered in the interior of the eye (25) in front of or behind this conjugate plane largely falls, on opaque interspaces between the holes of the Nipkow disk. Thus the Nipkow disk has a strongly depth-selective action.

In the further course of the beam, a pentaprism (35) with a ridge for image erection is arranged behind the Nipkow disk (31) and the beam splitter (30). The pentaprism (35) simultaneously deflects the beam path vertically downward. A beam splitter prism (36) is arranged to follow, and splits the beam path into two mutually parallel beam paths. The spacing of the two beam paths then corresponds exactly to the spacing of the two stereo channels (5a, 5b) (FIG. 1b) during operation as a stereo microscope. A further lens (37) is arranged between the pentaprism (35) and the beam splitter prism (36), and images the Nipkow disk at infinity. The full mirror (12) arranged on the rotary element (6) then deflects both parallel partial beam paths to the oculars (16). An observer looking into the oculars (16) now sees a binocular image of a defined plane within the subject's eye (25).

It is important that the deflection from the horizontal beam path (5) into the indirect beam path (26) running vertically upwards and also the deflection of the beam path (38) running vertically downwards by the mirrors (12, 13) take place within telecentric regions of the beam paths. By this means, it is ensured that no refocusing is necessary during a changeover from stereoscopic slit lamp observation to confocal microscopic observation.

Therefore the mirror (13), viewed from the subject's eye (25), is arranged immediately behind the main objective (4) and the deflecting mirror (12) is arranged immediately in front of the tube lens (14). Another lens (39) is arranged between the pentaprism (35) and the beam splitter prism (30). Due to its closeness to the Nipkow disk (31), which is in fact arranged in an intermediate image plane, the lens (39) acts mainly as a field lens. Its refractive power is chosen exactly such that the pupil of the main objective (4) on the observation side is imaged in the pupils of the oculars (16) via the indirect beam path (26) also.

Figure 2B:
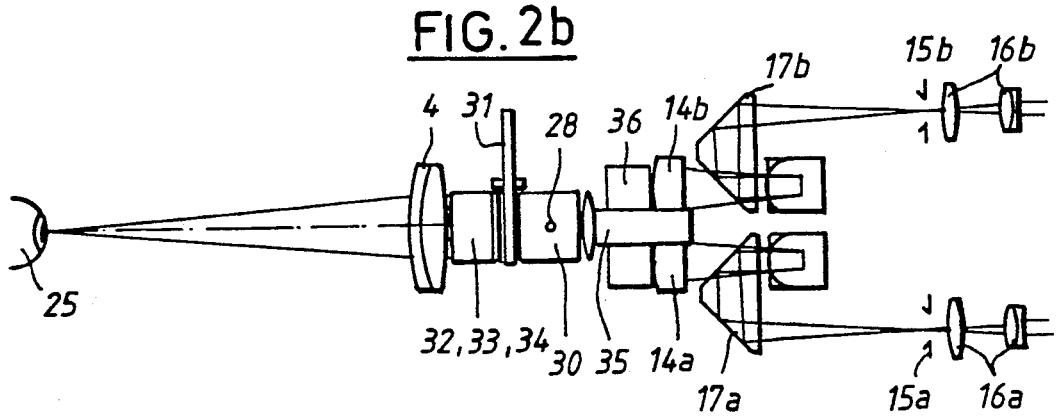
FIG. 2b is a schematic showing in principle the beam paths of the microscope of FIG. 2a, projected onto a horizontal plane.

The beam path during operation as a confocal perforated plate microscope is shown in FIG. 2b, projected onto a horizontal plane. Since the course of the beam in the indirect beam path (26) occurs predominantly in the vertical direction, many of the successive components, for example, the mirrors (13, 32) and also the teleobjective (33, 34), cannot be shown separately. Again, the same reference numbers are used here for identical components as in FIG. 2a. It is important for this embodiment that the stereo microscope is equipped with a common main objective (4), with the observation beam bundle running concentrically with the optical axis of the main objective during operation as a confocal perforated plate microscope. Because of this, the components arranged in the indirect beam path (26) between the splitter prism (36) and the main objective (4) need only be present singly. In this region, the beam paths for the left-hand ocular (16a) and the right-hand ocular (16b) run coaxially. Furthermore it is still important that the splitting into the two ocular beam paths by the splitter prism (36) takes place within a telecentric region. It is thus possible to present to the observer identical confocal images in both oculars (16a, 16b), which correspond to those of a confocal perforated plate microscope with binocular viewing. The changeover between stereoscopic observation on the one hand and confocal microscopic observation on the other hand takes place simply by the rotary element (6) (FIG. 1a, FIG. 2a) being brought into the corresponding switching position. Neither a refocusing nor a change of the ocular tube is necessary during this changeover. The ocular tube is moreover the same for both microscopy procedures. Since the changeover takes place quickly and easily, the observer can directly compare the images observed with the two microscopy procedures.

Figure 3:
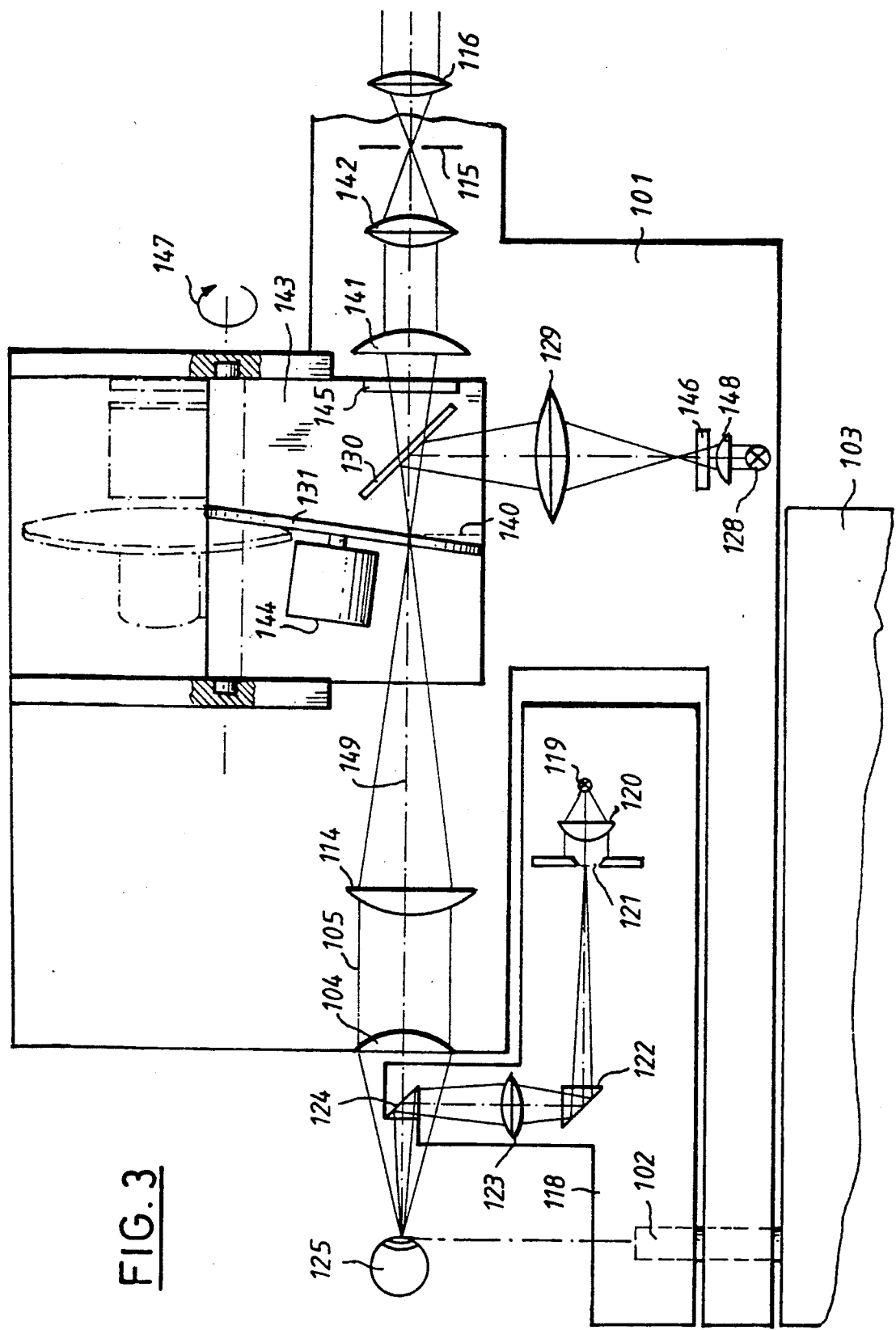
FIG. 3 is a vertical schematic through a second embodiment of the invention.

A second embodiment of the slit lamp microscope according to the invention is shown in FIG. 3. Those components that correspond to the previously described embodiment are shown with reference numbers increased by 100. The split lamp microscope again consists of a first housing portion (101), which contains the microscope, and a second housing portion (118), which contains the slit illumination means. Both housing portions (101, 118) are secured, rotatable about a common axis (102), to a base (103).

A light source (119) is provided within the slit lamp housing (118) and uniformly illuminates a slit (121) or a slit diaphragm through a collector (120). An image of the slit (121) is projected into the subject's eye (125) by means of two deflecting prisms (122, 124) and an interposed projecting system (123).

An infinity-corrected objective (104) is arranged in the microscope housing (101). The focal plane of this objective (104) coincides within the subject's eye with the plane in which the image of the slit (121) is projected. On the side of the objective (104) remote from the subject's eye (125), the observation beam path (105) at first runs telecentrically. A first tubular lens (114) produces intermediate images in a first intermediate imaging plane (140). An intermediate lens system (141, 142), constructed as a zoom lens system, images the first intermediate image plane (140) in a second intermediate image plane (115). The images in this second intermediate imaging plane (115) can be observed through oculars (116).

A Nipkow disk (131) including a drive motor (144) is arranged on a pivotable support element (143). At the same time, a further beam splitter (130) and a polarizer (145) are arranged between the intermediate image plane (140) and the transfer optics (141, 142). The whole system of Nipkow disk (131), beam splitter (130) and polarizer (145) can be moved out of the beam path by a pivoting motion of the support plate (143) in the direction of the arrow (147). The Nipkow disk (131), the beam splitter (130) and the polarizer (145) are then located in the position indicated by dot-dash lines. The pivoting plate (143) is latched in this upper change position by a locking device that is not represented in more detail here. This pivoted position of the pivoting plate (143) is provided for operating the microscope as a conventional slit lamp microscope. Illumination of the patient's eye then takes place via the light source (119) of the slit illumination means.

The light source (119) of the slit illumination means is switched out, and the additional light source (128) within the microscope housing (101) is switched in, when the Nipkow disk (131) is pivoted into the beam path by means of the support (143). A collector (148) arranged behind the light source and a lens (129) focus the light of the light source (128) in the intermediate image plane (140). The light transmitted through the transparent holes of the Nipkow disk (131) is focused by the tube lens (114) and the objective (104) into the subject's eye (125). An image of the Nipkow disk (131) thereby arises within the subject's eye (125). The light scattered or reflected within the subject's eye (125) is imaged by the objective (104) and the tube lens (114) in the intermediate image plane (140). Again, only that light can however be transmitted through the transparent holes of the Nipkow disk (131) that is scattered or reflected within the patient's eye (125) in a plane conjugate to the plane of the Nipkow disk (131). The Nipkow disk thus acts depth-selectively, in a known manner.

The Nipkow disk (131) itself consists, in a known manner, of opaque regions with numerous small transparent holes that are spirally arranged. The surface proportion of the transparent holes amounts to only a small percentage of the total surface of the Nipkow disk (131). Because of this relatively small proportion of transparent regions, the predominant portion of the light emitted by the light source (128) is reflected by the Nipkow disk (131). Two measures are taken in the microscope to prevent the disturbances due to these incident light reflections: firstly, the Nipkow disk (131) is not perpendicular to the optical axis (149), but is arranged slightly inclined to the optical axis such that the Nipkow disk (131) intersects the intermediate image plane (140). It is possible by means of this inclination to reflect the predominant portion of the incident light reflection out of the observation beam path. Regard must however be paid to the fact that due to the inclination between the Nipkow disk (131) and the optical axis (149), the plane conjugate to the Nipkow disk (131) is also correspondingly inclined to the optical axis (149) within the subject's eye (125), according to the Scheimpflug condition. For further suppression of the incident light reflection, a polarization filter (146) is arranged between the light source (128) and the beam splitter (130), and a second polarizer (145) is arranged between the beam splitter (130) and the transfer lens system (141, 142). The directions of polarization of both polarizers (146, 145) are aligned perpendicularly to each other, so that the light reflected on the Nipkow disk (131) is extinguished by the polarizer (145) in the observation beam path.

The arrangement of crossed polarizers (145, 146) in the illumination and observation beam paths has, still further, a second desired side-effect. Thus in addition to the incident light reflection at the Nipkow disk (131), the relatively strong corneal reflection of the subject's eye (125) is suppressed by the second polarizer (145). Since scattering, in contrast to reflection, has a strong depolarizing action, scattered light can thus be visually observed in defined planes of the subject's eye (125).

The transfer lens system (141, 142) arranged between the first intermediate image plane (140) and the second intermediate image plane (115) is constructed as a zoom lens system. The imaging scale on which the intermediate image plane (140) is imaged in the second intermediate image plane (115) is thus variable. Altogether, a variable total magnification thus also results.

Also, in the embodiment according to FIG. 3, a polarization beam splitter can be provided instead of the beam splitter (130), so that the whole of the light transmitted by the polarizer (146) is deflected to the Nipkow disk. With non-confocal observation, a glass cube which can be pivoted into the beam path is then to be provided, that effects the same longitudinal image offset as the corresponding polarization splitter cube in confocal observation.

I claim:
1. A slit lamp microscope comprising:
a slit lamp for projecting a slit-shaped spot of illumination in the eye of a subject,
a microscope with at least one objective, at least two oculars, and at least one beam path running between said objective(s) and said oculars, said beam path having an image in an intermediate image plane,
a diaphragm disk having a plurality of transparent and opaque regions, arranged in the region of said intermediate image plane in said beam path, said diaphragm disk being arranged to rotate to scan said image in said intermediate image plane and means for selectively moving said diaphragm disk into and out of said beam path.

2. A slit lamp microscope according to claim 1, wherein said diaphragm disk comprises a rotating Nipkow disk having several spiral paths along which said transparent regions re arranged.

3. A slit lamp microscope according to claim 1, further comprising a first housing portion in which said microscope is arranged, a second housing portion in which said slit lamp is arranged and means for rotating said first and said second housing portions about a common axis in the focal plane of said microscope objective.

4. A slit lamp microscope comprising:
a slit lamp for projecting a slit-shaped spot of illumination in the eye of a subject,
a microscope with at least one objective, at least two oculars, and at least one beam path running between said objectives(s) and said oculars, said beam path having an image in an intermediate image plane,
a diaphragm disk having a plurality of transparent and opaque regions, arranged in the region of said intermediate image plane in said beam path, said diaphragm disk being arranged to rotate to scan said image in said intermediate image plane,
additional beam paths in said microscope, and
means for alternately switching to said additional beam paths for normal slit lamp observation and to said beam path for observation through said diaphragm disk.

5. A slit lamp microscope according to claim 4, further comprising an additional illumination device and reflecting means for directing light from said additional illumination device along said optical path, between said diaphragm disk and said oculars.

6. A slit lamp microscope according to claim 5, wherein said reflecting means comprises a partially reflecting mirror, further comprising means for simultaneously moving said diaphragm disk and said partially reflecting mirror into said beam path.

7. A slit lamp microscope according to claim 6, further comprising means for driving said diaphragm disk and an element on which said diaphragm disk, said driving means and said partially reflecting mirror are arranged.

8. A slit lamp microscope according to claim 7, wherein said microscope is a stereo microscope.

9. A slit lamp microscope according to claim 8, wherein light from said additional illumination device is linearly polarized, further comprising a polarizer arranged between said diaphragm disk and said oculars, having a direction of transmission perpendicular to the polarization of the light reflected into said beam path.

10. A slit lamp microscope according to claim 4, wherein said microscope is a stereo microscope and said additional beam paths comprise stereo channels of said stereo microscope.

11. A slit lamp microscope according to claim 10, wherein said means for alternately switching to said additional beam paths and to said beam path are arranged on a rotary element rotatable about an axis lying perpendicular to said additional beam paths.

12. A slit lamp microscope according to claim 11, further comprising additional optical elements arranged on said rotary element for selective movement into said additional beam paths.

13. A slit lamp microscope according to claim 12, wherein said additional optical elements comprise paris of lens systems that pairwise form Gallilean telescopes.

14. A slit lamp microscope according to claim 4, wherein said diaphragm disk comprises a rotating Nipkow disk having several spiral paths along which said transparent regions are arranged.

15. A slit lamp microscope comprising:

a slit lamp for projecting a slit-shaped spot illumination in the eye of a subject, a microscope with at least one objective, at least two oculars, and at least one beam path running between said objective(s) and said oculars, said beam path having an image in an intermediate image plane, a diaphragm disk having a plurality of transparent and opaque regions, arranged in the region of said intermediate image plane in said beam path, said diaphragm disk being arranged to rotate to scan said image in said intermediate image plane, additional beam paths in said microscope, means for alternately switching to said additional beam paths for normal slit lamp observation and to said beam path for observation through said diaphragm disk, an additional illumination device, and reflecting means for directing light form said additional illumination device along said beam path between said diaphragm disk and said oculars, wherein light from said additional illumination device is linearly polarized, further comprising a polarizer arranged between said diaphragm disk and said oculars, having a direction of transmission perpendicular to the polarization of light reflected into said beam path.

* * * * *